(12) United States Patent
Eidenberger (10) Patent No.: US 8,128,970 B2
(45) Date of Patent: Mar. 6, 2012

(54) SESAME SEED DERIVED PIGMENTS

(75) Inventor: Thomas Eidenberger, Steyr (AT)

(73) Assignee: Omnica GmbH, Hamburg (DE)

( * ) Notice: Subject to any disclaimer, the term of this patent is extended or adjusted under 35 U.S.C. 154(b) by 116 days.

(21) Appl. No.: 12/510,395

(22) Filed: Jul. 28, 2009

(65) Prior Publication Data

US 2010/0028474 A1 Feb. 4, 2010

Related U.S. Application Data

(60) Provisional application No. 61/083,994, filed on Jul. 28, 2008.

(51) Int. Cl.
*A01N 65/00* (2009.01)
(52) U.S. Cl. ..................... 424/725
(58) Field of Classification Search ............... None
See application file for complete search history.

(56) References Cited

U.S. PATENT DOCUMENTS

| | | | |
|---|---|---|---|
| 4,649,206 | A | 3/1987 | Namiki et al. |
| 4,708,820 | A | 11/1987 | Namiki et al. |
| 4,847,106 | A | 7/1989 | Pike et al. |
| 2004/0121058 | A1 | 6/2004 | Jayalekshymy et al. |
| 2008/0089906 | A1 | 4/2008 | Rival et al. |

FOREIGN PATENT DOCUMENTS

| | | | |
|---|---|---|---|
| JP | 10279497 | * | 10/1998 |
| WO | WO 93/21252 | | 10/1993 |
| WO | WO 01/18125 | | 3/2001 |

OTHER PUBLICATIONS

International Search Report PCT/EP2009/059775 dated Apr. 13, 2010.
Vagabhata; Astanga Hrdaya—(commented by Arunadutta) edited by Bhisagacarya Harisastri Paradakara vaidya: Chaukhamba Orientalia, Varanasi, Edn. $8^{th}$, 1988 [Time of origin $5^{th}$ century] p. 687, Sunthyadi Curna.
Rasatantrasarah Evam Siddhaprayogasamgraha; part II; Krishan Gopal Ayurveda Bhawan; Edn. $8^{th}$; 1990 [This book contains back references from 1000 B.C, to $20^{th}$ century] p. 473-476, Pathya Bhallataka Modaka.
Mohammad Akbar Arzani; Qaraabaadeen Qaadri ($17^{th}$ century AD), Ahmadi Publication, Delhi, 1968 AD, p. 144, Muffarreh Dilkusha-e-haar.
Kaiyadeva; Kaiyadevanighantau—(Pathyapathyavibodhakah) Edited and translated by P.V. Sharma and Guru Prasad Sharma, Chaukhambha Orientalia, Varanasi, Edn. $1^{st}$, 1979, p. 415-416, Kambalikayusah.
Brhat Nighantu Ratnakara—compiled by Gangavisnu Srikrsna Dasa, Translated by Sri Dattarama Srikrsnalala Mathura; vol. 3 (Part V), Edn. 1996, Khemaraja Srikrsnadas Prakasana, Mumbai-4 [This book contains back references from 1000 B.C. to $20^{th}$ century] p. 666, Gudadimodaka.
Bhavamisra; Bhavaprakasa—Edited & translated by Brahmasankra Misra, Part II: Chaukhamba Sanskrit Sansthan, Varanasi, Edn. $7^{th}$, 2000 [Time or origin $16^{th}$ century] p. 329, Sunthyadikalkam.
Vangasena; Vangasena—Commentator Shaligram Vaisya, Edited Shankar Ialji Jain; Khemraj Shrikrishna Das Prakashan, Bombay, Edn. 1996, p. 234, Satapaka Taila.
Brhat Nighantu Ratnakara—Compiled by Gangavisnu Srikrsna Dasa, Translated by Sri Dattarama Srikrsnalala Mathura; vol. 1 (Part III), Edn. 1995, Khemaraja Srikrsnadas Prakasana, Mumbai-4 [This book contains back references from 1000 B.C. to $20^{th}$ century] p. 607, Kambalikayusah (2).
Bharata Bhaisajyo Ratnakara—Compiled by Naginadasa Chaganalala Saha, Translared by Gopinath Gupta—vol. III: B. Jain Publishers, New Delhi, Edn. $2^{nd}$ Reprint, Aug. 1999, [This book contains back references from 1000 B.C. to $20^{th}$ Century] p. 630, Bhrngarajarasayanam (02).
S.S. Sawhney, "Thermal Stability of Melanin", Termochimaica Acta 247, 1994, pp. 377-380.
Howard S. Mason "Mechanism of the Oxidation of Dihydroxyphenylalanine by Tyrosinase", The Chemistry of Malanin, III, The Journal of Biological Chemistry, May 1, 1997, pp. 83-99.
F. Shahidi, et al., "Antioxidant Activity of White and Black Sesame Seeds and Their Hull Fractions", Food Chemistry 99, 2006, pp. 478-483.

* cited by examiner

*Primary Examiner* — Michael Meller
(74) *Attorney, Agent, or Firm* — Scott D. Rothenberger; Fulbright & Jaworski (57) ABSTRACT

The invention describes reduced sesame seed derived pigments and methods to prepare such pigments.

13 Claims, 4 Drawing Sheets

Determination of the molecular weight by Gel Permeation Chromatography
Test Sample:    Sesame Pigment (TEI V2)

Column:         Shodex 802.5 300 x 4.9 mm
Flow rate:      1 ml/min
Mobile Phase:   THF
Detection:      280 nm Arrows and numbers indicate molecular weight markers.

SESAME SEED DERIVED PIGMENTS

CROSS REFERENCE TO RELATED APPLICATIONS

This application claims benefit under 35 U.S.C. §119(e) to U.S. Patent Application Ser. No. 61/083,994, entitled "Sesame Seed Derived Pigments", filed Jul. 28, 2008, the contents of which are incorporated herein in their entirety for all purposes.

FIELD OF THE INVENTION

The invention relates generally unique materials extracted primarily from sesame seed shells.

BACKGROUND OF THE INVENTION

Melanin is a class of compounds found in plant, animal and protista kingdoms, where it serves predominantly as a pigment. The class of pigments are derivatives of the amino acid tyrosine. The most common form of biological melanin is eumelanin, a brown-black polymer of dihydroxyindole (also known as hydroquinone) and dihydroxyindole carboxylic acid. Another common form of melanin is pheomelanin, a red-brown polymer of benzothiazine units largely responsible for red hair and freckles. Due to the complex nature of melanin, the exact chemical make up of the various types of melanin are still under investigation.

Both pheomelanin and eumelanin are found in human skin and hair, but eumelanin is the most abundant melanin in humans.

Eumelanin polymers have long been thought to comprise numerous cross-linked 5,6-dihydroxyindole (DHI) and 5,6-dihydroxyindole-2-carboxylic acid (DHICA) polymers. However, the precise nature of eumelanin's molecular structure has not been identified. Eumelanin is found in hair and skin, and colors hair grey, black, yellow, and brown.

Pheomelanin is also found in hair and skin and is both in lighter skinned humans and darker skinned humans. In general women have more pheomelanin than men, and thus women's skin is generally redder than men's. Pheomelanin imparts a pink to red hue and, thus, is found in particularly large quantities in red hair.

Melanin is considered an effective radical scavenger.

Deficiencies of melanin can lead to Parkinson's disease, Alzheimer's disease, retinitis pigmentosa, xeroderma pigmentosum, schizophrenia and dementia.

Increased melanin levels can help increase darkening of hair color thus reducing the amount of grey hair associated with aging.

Therefore, a need exists for improved melanin like agents that help to remedy one or more of the above-identified conditions.

BRIEF SUMMARY OF THE INVENTION

The present invention surprisingly provides a sesame extract and methods to prepare the sesame extract that are useful to treat an assortment of various ailments or conditions described herein. The sesame extracts provide materials that can be used to help stabilize other materials, such as coenzyme Q10, DHA, vitamins, such as vitamin C, etc. that are subject to oxidation.

A representation of the reduced melanin can be depicted by formula (I)

wherein each X, of each m and n unit, independently, can be either a COOH or salt thereof or a hydrogen atom;

wherein at least one of each $Y^1$ or each $Y^2$, of each m and n unit, independently, is an NH and the other is a CH provided both $Y^1$ and $Y^2$ are not both NH or CH;

wherein each $Q^1$ and $Q^2$, of each m and n unit, are each independently, a hydroxyl, a hydroxyl anion, a H, or a =O;

provided that the molar ratio of hydroxyl to ketone functionality, if present, within the reduced melanin is greater than 50 percent, more particularly 60 percent, even more particularly 75 percent, and in particular at least about 80 percent;

wherein ===== represents a conjugated π system; and wherein m is from 1 to about 40;

wherein n is from 1 to about 40;

wherein m+n=from 2 to about 40, more particularly from about 3, 4, 5, 6, 7, etc. to about 40, and all ranges and integers therein between, wherein each monomeric indolic unit of each individual "m" and each individual "n" can be the same or different.

In one aspect, the monomeric units of "m" and "n" are random throughout the oligomeric/polymer structure of the reduced melanin oligomer or polymer. This should include random polymeric/oligomeric materials as well as block materials.

In another aspect, the monomeric units of "m" and "n" do not vary and are a random oligomer/polymer of two monomeric units.

In still another aspect, the monomeric units of "m" and "n" can be the same, e.g., the same monomeric unit is oligomerized/polymerized in both "m" and "n" portions of the oligomer or polymer.

In one aspect, at least one of $Q^1$ or $Q^2$ is a hydroxyl or represent an oxygen (=O).

In another aspect, the UV-VIS absorbance of the sesame extract from sesame is about 0.1 to about 0.16 at 500 nm at a concentration 0.04 mg/ml in a aqueous solution.

In another aspect, n can be equal to 1 and it can be useful to treat the various afflictions noted throughout the specification. When n=1, it is possible that the monomer (which can be the basis for the oligomeric/polymeric forms of the reduced melanin) can have the formula:

and has a molecular weight of 133.

In one aspect the present invention provides sesame extracts comprising a reduced melanin wherein the molecular weight of the reduced melanin is between about 264 and about 5400 daltons, the carbon content of the reduced melanin is between about 35 percent and about 57 percent by weight, the hydrogen content of the reduced melanin is between about 5 percent and about 10 percent by weight and the nitrogen content is between about 5 and about 10 percent by weight. The oxygen content, if present, of the reduced melanin is between about 33 percent and about 37 percent by weight, and the ratio of hydroxyl to carbonyl quinone content of the reduced melanin is at least 50 percent (hydroxyl to ketone carbonyl) on a molar basis.

Generally, the reduced melanin pigment is derived from a seed shell or hull particularly from a sesame seed.

In one aspect, the nitrogen content of the reduced melanin is between about 5 percent and about 10 percent by weight.

In another aspect, the sulfur content of the reduced melanin is less than about 1 percent by weight.

In still another aspect, the infrared spectra of the reduced melanin exhibits absorption bands at about 3400 cm$^{-1}$ (phenolic —OH stretches), at about 2950 cm$^{-1}$ (aliphatic stretches), at about 1600 to about 1650 cm$^{-1}$ (aromatic C=C stretches), at about 1380 to about 1400 cm$^{-1}$ (phenolic C—OH, indolic and phenolic NH stretches), at about 1260 cm$^{-1}$ (phenolic COH) and at about 1170 cm$^{-1}$ (C=O stretches).

In still yet another aspect, the molecular weight range of the reduced melanin is between about 264 and about 2000 daltons.

In another aspect the molecular weight range of the reduced melanin is between about 400 and about 1600 daltons.

The present invention also provides a method to prepare a sesame extract. The method includes mixing an aqueous base (pH above about 10, for example between about 10 and about 14, and for example, a pH of about 12) and pulverized sesame seed at an elevated temperature followed by cooling of the mixture to room temperature. The resultant mixture is filtered and rinsed with water to provide a filtrate. The filtrate and rinse solutions are treated with an aqueous base and a reducing agent is added to the filtrate until evolution of gas ceases and the reduced melanin pigment is formed.

The present invention also provides an alternative method to prepare a sesame extract. The method includes mixing an aqueous base (pH above about 10, for example between about 10 and about 14, and for example, a pH of about 12) and pulverized sesame seed at or below room temperature. The mixture is filtered and rinsed with water to provide a filtrate. The filtrate is treated with an aqueous acid at or below room temperature to a pH of below about 4 and generally a pH between about 1 and about 2. The resultant sesame extract is collected.

The sesame extract can be used as a nutritional supplement, to help increase coloration in hair, to help improve liver function, to help increase lutein in the eye (so as an eye protectant) to help diminish or ameliorate retinitis pigmentosa or xeroderma pigmentosum, for treatment of the nervous system by lowering the concentration of free radicals in the brain as an antioxidant and nutritional supplement for the nervous system, brain and bone marrow health, for degenerative diseases such as Parkinson's disease, Alzheimer's disease, enhancing or maintaining cognition, schizophrenia and dementia, as a skin protectant (UV protection, photoprotectant), for metal chelation, as a radical scavenger, as a method to reduce or inhibit the oxidation of LDL, as a method to treat cardiovascular diseases, such as atherosclerosis, or coronary artery disease, as a method to treat or prevent ulceration and as an antioxidant.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of"

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a reduced melanin into the body, preferably into the systemic circulation. Examples include but are not limited to oral, buccal, sublingual, pulmonary, transdermal, transmucosal, as well as subcutaneous, intraperitoneal, intravenous, and intramuscular injection.

The term "carrier" is intended to include any material, liquid or solid, that can be utilized to administer the sesame extracts of the invention. This can include emulsions, suspensions, liquids, and food products and described herein.

The sesame extract can be administered in a therapeutically effective amount via a pharmaceutically acceptable method.

The term "therapeutically effective amount" is intended to mean an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. The preparation can be enclosed in ampoules, disposable syringes or multiple dose vials made of glass or plastic.

These compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the sesame extract of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test bioassays or systems.

Administration of the doses recited above can be repeated. In one embodiment, the doses recited above are administered 1 to 7 times per week. The duration of treatment depends upon the patient's clinical progress and responsiveness to therapy.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

"Food" or "food product" refers to any solid or liquid edible substance that can be consumed by a subject. Such food products include baked goods, snack foods (candy, gum, candy bars, etc.), dairy products (ice cream, yogurt) and beverages (soda, milk, coffee, tea, etc.) and beverage mixes.

The term "melanin" is known in the art and encompasses polymeric materials described as in the book entitled "Melanins," by R. A. Nicolaus, published in 1968 by Hermann, 115, Boulevard Saint-Germain, Paris, France, which work in its entirety is incorporated herein by reference. Generally, melanin is recognized as an irregular light absorbing polymer that contains indoles and other intermediate products derived from the oxidation of tyrosine. The basic structural unit of melanins is usually represented by covalently linked indoles. It must be emphasized that the overall structure of melanin is not known. Most melanins appear to be mixed polymers based on indoles but can contain varying amount of other pre-indolic products of the melanin biosynthetic pathway. Molecular weights of the melanin are generally from about 10,000 daltons and greater. A representative structure is noted below:

The term "reduced melanin" refers to a melanin containing material, generally the shell or husk of a seed, that is treated under conditions to reduce the majority of carbonyl (ketone/ortho-quinone) content of the melanin to hydroxyl functionality. Generally, this means that the molar ratio of hydroxyl to remaining ketone functionality (if any remains) within the reduced melanin is greater than 50 percent, more particularly 60 percent, even more particularly 75 percent, and in particular at least about 80 percent.

In one aspect, the reduced melanin is devoid of hydroxyl or ketone functionality.

A representation of the reduced melanin can be depicted by formula (I)

wherein each X, of each m and n unit, independently, can be either a COOH or salt thereof or a hydrogen atom;
wherein at least one of each $Y^1$ or each $Y^2$, of each m and n unit, independently, is an NH and the other is a CH provided both $Y^1$ and $Y^2$ are not both NH or CH;
wherein each $Q^1$ and $Q^2$, of each m and n unit, are each independently, a hydroxyl, a hydroxyl anion, a H, or a =O;
provided that the molar ratio of hydroxyl to ketone functionality, if present, within the reduced melanin is greater than 50 percent, more particularly 60 percent, even more particularly 75 percent, and in particular at least about 80 percent;
wherein ===== represents a conjugated π system; and
wherein m is from 1 to about 40;
wherein n is from 1 to about 40;
wherein m+n=from 2 to about 40, more particularly from about 3, 4, 5, 6, 7, etc. to about 40, and all ranges and integers therein between, wherein each monomeric unit of "m" and "n" may be the same or different.

In one aspect, at least one of $Q^1$ or $Q^2$ is a hydroxyl or represent an oxygen (=O).

In certain aspects, n can be 1.

When n=1, it is possible that the monomer (which can be the basis for the oligomeric/polymeric forms of the reduced melanin of the invention discussed herein) can have the formula:

and has a molecular weight of 133.

Possible monomeric units of the oligomer/polymer include those described throughout the specification as well as:

wherein X is COOH, a salt thereof, or a hydrogen atom.

It should be understood that the reduced melanin pigment can be a homopolymer or oligomer of a particular monomeric unit described herein. Alternatively, the oligomer or polymer of the reduced melanin pigment can contain two or more monomeric units described herein.

It should also be understood that the terminal indolic ends of the reduced melanin pigment oligomer/polymer would terminate with a hydrogen at the otherwise respective site for attachment to another monomeric unit.

The pigment, as an active ingredient, comprises a polymeric or oligomeric substance. The polymer or oligomer is an indolic material, which can be linked at 4- and 7-positions. The 5- or 6-position of indole portion of the material can be independently substituted with a hydroxyl, a hydroxyl anion, a hydrogen atom (H) or a =O (as a carbonyl group for ketone functionality); the 2-position of indole part can be substituted with either —COOH or salt thereof or a hydrogen atom. In view of indole, the material has a conjugated π system, at least partially.

In the polymer or oligomer of the invention, the molar hydroxyl content is higher than the starting melanin material. Generally, the molar ratio of hydroxyl to ketone functionality, if present, within the reduced melanin, is greater than 50 percent, more particularly 60 percent, even more particularly 75 percent, and in particular at least about 100 percent.

In the polymer or oligomer of the invention, each monomeric unit of the material is an indolic compound. These repeating units (indolic compounds) can be the same or different. Monomer units in the present invention can be any of below structures at random.

For example, in one aspect, the polymer or oligomer can be represented by a conjugated system noted below (which shows the inclusion of each of the monomeric units noted above).

wherein X is COOH, a salt thereof, or a hydrogen atom.

Furthermore, the polymer or oligomer in the present invention can be a polymer comprising several independent conjugated fractions. This kind of complex polymer has also the same function.

The polymer or oligomer of the present invention can include additional group(s), such as esters, ethers, alkyl groups, etc.

In addition, the carbon-carbon bond between two indolic units can be replaced by an alkyl chain, etc.

In another aspect, the reduced melanin material can be depicted by formula (II)

(II)

wherein X can be either a COOH or salt thereof or a hydrogen atom;

wherein at least one of $Y^1$ or $Y^2$ is an NH and the other is a CH, provided that both $Y^1$ and $Y^2$ are not both NH or CH;

wherein $Q^1$ and $Q^2$, are each independently, a hydroxyl, a hydroxyl anion, a H or a =O;

provided that the molar ratio of hydroxyl to ketone functionality, if present, within the reduced melanin is greater than 50 percent, more particularly 60 percent, even more particularly 75 percent, and in particular at least about 100 percent;

wherein ===== represents a conjugated π system; and wherein n is at least 2 to about 40, more particularly from about 3, 4, 5, 6, 7, etc. to about 40, and all ranges and integers therein between.

It should be understood that the monomeric indolic units within such a oligomer or polymer can the be same or different.

In another aspect, the sesame extract can be characterized by having a UV-VIS spectrum with an absorbance between about 0.1 to about 0.16 at 500 nm at a concentration at less than 0.04 mg/ml in an aqueous solution.

The reduced melanin pigment has a molecular weight of between about 264 and about 5400 daltons, more particularly between about 264 and about 2000 daltons, even more particularly between about 400 and about 1600 daltons, more particularly between about 264 and about 1600 daltons, more particularly between about 532 and 1064 daltons, and all ranges therebetween from about 264 to about 5400 daltons.

The reduced melanin pigment can be characterized by the elemental composition of the reduced melanin. The carbon content of the reduced melanin is between about 35 percent and about 57 percent by weight, the hydrogen content of the reduced melanin is between about 5 percent and about 10 percent by weight and the nitrogen content is between about 5 and about 10 percent by weight. The oxygen content, if present, of the reduced melanin is between about 33 percent and about 37 percent by weight.

In one aspect, the nitrogen content (if present) of the reduced melanin is between about 5 percent and about 10 percent by weight.

In another aspect, the sulfur content (if present) of the reduced melanin is less than about 1 percent by weight.

The black sesame seed useful in the invention is the seed from the plant *Sesamum indicum*. Generally, the reduced melanin pigment is derived from a seed shell or hull particularly from a sesame seed that includes melanin. Alternatively, twigs, bark, branches, leaves and/or roots to the sesame plant can be used to obtain the starting material melanin. The seed shell or hull of the black sesame seed is most abundant with the desired melanin used to provide the reduced melanin.

In one aspect the reduced melanin of the present invention has an infrared spectra that exhibits distinctive absorption bands at 3400 $cm^{-1}$ (phenolic —OH stretches), at about 2950 $cm^{-1}$ (aliphatic stretches), at about 1600 to about 1650 $cm^{-1}$ (aromatic C=C stretches), at about 1380 to about 1400 $cm^{-1}$ (phenolic C—OH, indolic and phenolic NH stretches), at about 1260 $cm^{-1}$ (phenolic COH) and at about 1170 $cm^{-1}$ (C=O stretch).

The sesame extract of the present invention has many uses noted throughout this specification including one or more of the following. The reduced melanin can be used as a nutritive supplement, such as a component of a plant food. The reduced melanin can be utilized in the food industry as an ingredient of a food or beverage, such as in ice-cream or yogurt.

The sesame extract of the present invention can be used for the protection of lutein, coenzyme Q10 or DHLA, DHA, vitamins, such as vitamin C, phosphorylcholine, etc. from oxidation or degradation.

The sesame extract of the present invention can be used as a hair supplement, such as for blackening hair and/or as nutraceutical/functional food. Long term of consumption of the reduced melanin can be regarded as an effective measure for personal hair care.

The sesame extract of the invention can be used for eye protection. The use of the reduced melanin can help maintain the concentration of lutein in the eyes and produce a positive effect to eye health or vision care as a supportive therapy. Therefore, the material can be used to treat or prevent such conditions.

The sesame extract of the invention is useful for nervous system conditions, such as lowering the concentration of free radicals in brain tissue. This can be considered an antioxidant and/or as a nutritional supplement for the nerve, brain, and marrow health. Therefore, the material can be used to treat or prevent such conditions.

The sesame extract of the invention can be useful for treating or preventing degenerative diseases of the nervous system, such as Parkinson's disease, Alzheimer's disease, enhancing or maintaining cognition, etc.

The sesame extract of the invention can be used for skin protection, such as UV protection and photo-protection.

The sesame extract of the invention can be used in combination with the derivatives of salicylic acid or salicylates, such as aspirin (acetylsalicylic acid), derivatives of aspirin or salicylic acid, such as sodium salicylate, etc, to prevent or alleviate the pain from ulceration caused by the administration of the derivatives of salicylic acid or salicylates. Willow bark extract can be considered a derivative of salicylic acid, and therefore, can be used in combination with the sesame extract of the invention.

The present invention also provides methods to prepare a sesame extract. The methods include mixing an aqueous base and pulverized sesame seed at an elevated temperature followed by cooling of the resultant mixture to room temperature. The resultant mixture is filtered and rinsed with water to provide a filtrate. The filtrate is treated with an aqueous acid and a reducing agent is added to the filtrate until evolution of gas ceases and the sesame extract is formed.

The concentration of the base in the aqueous base is between about 0.5 percent and about 2 percent by weight. Suitable bases include amines and various metal hydroxides, such as potassium hydroxide and sodium hydroxide. Generally the ratio of aqueous base to sesame seed is about 5:1 on a weight basis and generally the elevated temperature of the first step is between about 40° C. and about 80° C., e.g., 60° C. The mixture is generally heated for between about 0.5 hours and about 5 hours, e.g., 3 hours.

The treated filtrate of the process is agitated (e.g., stirred or sonicated) prior to addition of the reducing agent. Suitable reducing agents include dihydrolipoic acid, sodium borohydride, or other reducing agents having an —SH group. The reducing agent is added to the filtrate at temperature between about 10° C. and about 35° C., more particularly at about 25° C.

The present invention also provides an alternative method to prepare a reduced melanin pigment (sesame extract). The method includes mixing an aqueous base and pulverized sesame seed at or below room temperature. The mixture is filtered and rinsed with water to provide a filtrate. The filtrate is treated with an aqueous acid at or below room temperature to a pH of between about below 7 and a pH of about 1. The resultant reduced melanin pigment collected.

The concentration of the base in the aqueous base in step is between about 0.5 percent and about 2 percent by weight (pH above about 10, for example between about 10 and about 14, and for example, a pH of about 12). Suitable bases include amines and various metal hydroxides, such as potassium hydroxide and sodium hydroxide. Generally the ratio of aqueous base to sesame seed is about 5:1 on a weight basis and generally the temperature of the mixture is maintained below about 35° C., e.g., 25° C. The mixture of step a) is mixed for between about 0.5 hours and about 48 hours, for example, about 24 hours.

The aqueous acid can be any organic or mineral acid, such as acetic acid, hydrochloric acid, sulfuric acid, nitric acid, or phosphoric acid is about 15% acid by volume. The temperature of the filtrate is maintained below about 35° C., for example, 25° C. during and after the addition of the acid solution. Generally the pH is lowered below a pH of 7 and in particular to a pH of about 1.

The resultant reduced melanin pigment can be collected by various methods such as filtrations or by centrifugation.

The following examples are illustrative in nature and should not be considered limiting in any way.

EXAMPLES

Example 1

5 g sodium hydroxide were dissolved in 500 ml de-ionized water, and then added to 100 g pulverized black sesame seed. The mixture was stirred and heated to 60° C. The reaction mixture was maintained at 60° for 3 hours and then cooled to room temperature. The black mixture was filtered and the filter cake was washed with 100 ml de-ionized water. The filtrate and rinse solution was treated with an aqueous acid solution (pH about 1). The solution was sonicated for 10 minutes at a temperature of 25° C. Potassium borohydride was added slowly while maintaining the reaction temperature below or at 25° C. The mixture was allowed to stand for about 25 minutes until gas evolution ceased. The potassium borohydride can be replaced by other reducing agents, such as DHLA. Potassium borohydride can be removed by water washes. DHLA can be removed by washing the product with ethanol. This sample is referred to as Product of Example 1 in the Determination of Sesame pigments with UV-VIS absorption below.

Example 2

5 g sodium hydroxide was dissolved in 500 ml de-ionized water, cooled to room temperature, and then 100 g pulverized black sesame seed was added. The temperature of the reaction mixture was maintained below 25° C., stirred for 24 hours and filtered. The filter cake was washed with 100 ml de-ionized water. The filtrate and rinse solutions were combined and acidified with 15% hydrochloride solution, maintaining the temperature of the reaction mixture below 25° C. with a final pH is about 1.0. The suspension was centrifuged and the solids were washed with 30 ml de-ionized water. The solid materials was vacuum dried to afford about 1 g black reduced sesame pigment. (It was found that the UV absorption coefficient is lower than the starting material and can protect lutein in water micelles.) This sample is referred to as Product of Example 2 in the Determination of Sesame pigments with UV-VIS absorption below.

Example 3

TEI V1

5 g sodium hydroxide was dissolved in 500 ml de-ionized water, cooled to room temperature, and then 100 g pulverized black sesame seed was added. The temperature of the reaction mixture was maintained below 25° C., stirred for 24 hours and filtered. The filter cake was washed with 100 ml de-ionized water. The filtrates were combined and acidified with 15% hydrochloride solution, maintaining the temperature of the reaction mixture below 25° C. with a final pH is about 1.0. The suspension was centrifuged and the solids were washed with 30 ml de-ionized water. The product was collected and vacuum dried (−0.095 MPa, 60° C., for 4 hours) followed by desiccation over $P_2O_5$. The dried pigment was washed with petroleum ether and again dried. Yield of reduced melanin pigment was about 5% based on initial starting material. This sample is referred to as Product of Example 3 in the Determination of Sesame pigments with UV-VIS absorption below.

Figure 1:
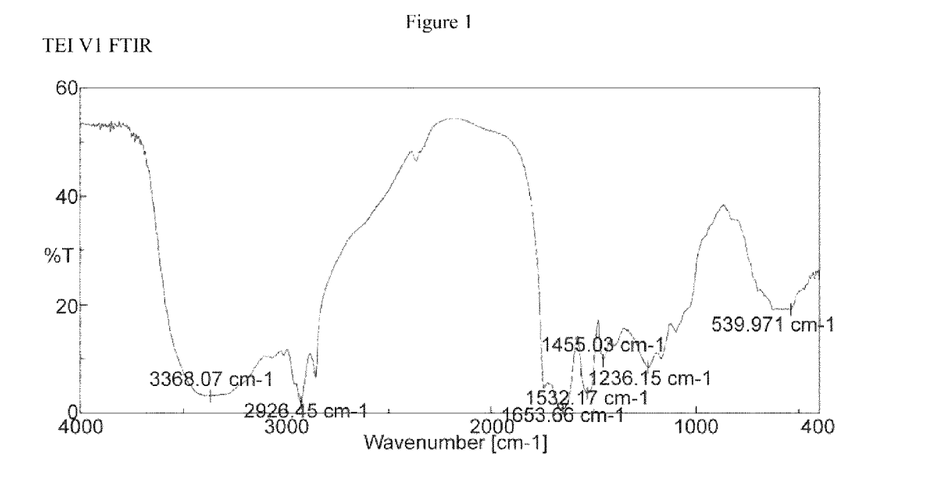
FIG. 1 is an FTIR of the isolated product TEI V1 of Example 3.

FIG. 1 is an FTIR of the isolated product TEI V1.

Example 4

TEI V2

10 g of pulverized black sesame seed was suspended in 50 ml of 20% aqueous glycerol and 0.9% NaOH. The mixture was stirred for 24 hours and filtered, then washed with petroleum ether. The filtrate and washes were acidified with 15% hydrochloride solution, maintaining the temperature of the reaction mixture below 25° C. with a final pH is about 1.0. The suspension was centrifuged and the solids were washed with 30 ml de-ionized water. The product was collected and vacuum dried (−0.095 MPa, 60° C., for 4 hours) followed by desiccation over $P_2O_5$. Yield of reduced melanin pigment was about 3% based on initial starting material. This sample is referred to as Product of Example 4 in the Determination of Sesame pigments with UV-VIS absorption below.

Figure 2:
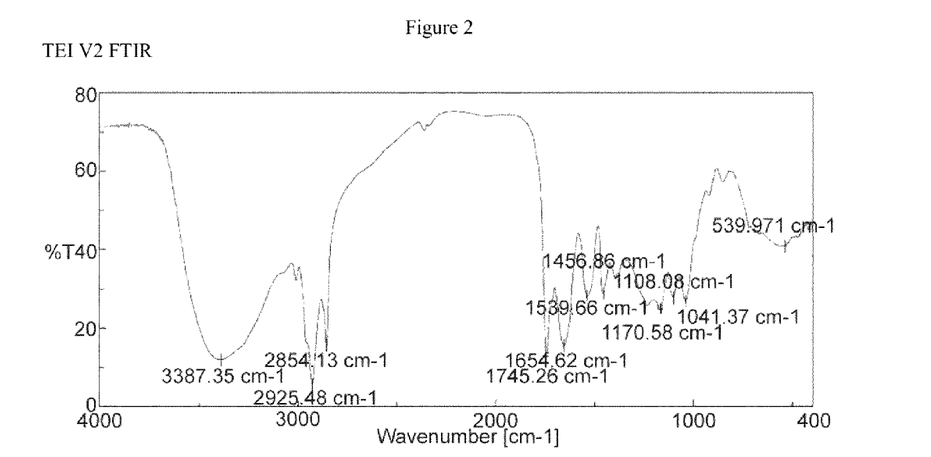
FIG. 2 is an FTIR of the isolated product TEI V2 of Example 4.

FIG. 2 is an FTIR of the isolated product TEI V2.

Figure 3:
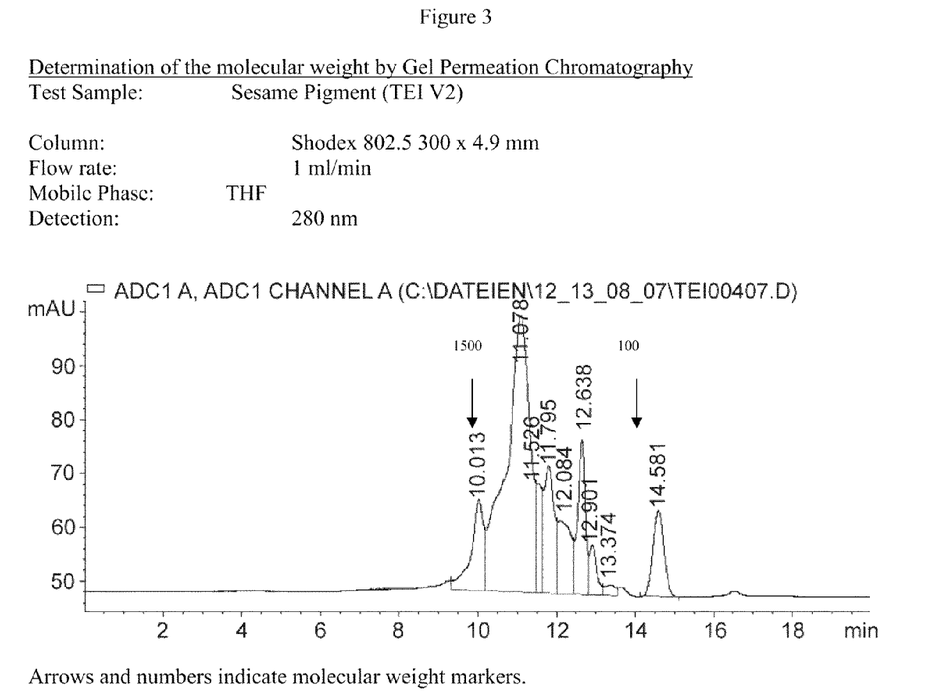
FIG. 3 depicts the molecular weight by Gel Permeation Chromatography of sample TEI V2 of Example 4.

FIG. 3 depicts the molecular weight by Gel Permeation Chromatography of sample TEI V2.

Example 5

The present example indicates the reduced sesame pigment protects lutein from degradation.

In a 10 ml volumetric flask, 10 mg lutein was dissolved in 5.0 ml tetrahydrofuran (THF), then filled to volume with absolute ethanol.

To a small beaker, was added 0.5 g Tween-80 and 15 g de-ionized water. The solution was stirred until homogeneous and then 2 mg reduced sesame melanin was added (Example 1) The mixture was sonicated until the solution become clear.

1.0 ml of the above lutein solution was added to the small beaker and slightly shaken to dissolve the lutein. 1.0 ml liquid from the small beaker was transferred to a 10 ml volumetric flask and filled to volume with de-ionized water.

A blank sample was prepared as above without addition of the reduced sesame pigment solution.

The lutein/reduced sesame sample and blank sample were both put into a 37° C. water bath and exposed to a 15 W lamp for 3 hours. The absorbance was measured at 446 nm with a UV-Visible spectrophotometer to determine the degradation rate.

The residual ratio of the lutein samples are provided in the table below.

| Sample name | Residual ratio of lutein/% |
|---|---|
| Blank Sample | 80.9 |
| Reduced sesame pigment | 94.9 |

Example 6

The following example indicates that the reduced melanin pigment can protect DHA from degradation.

25 mg DHA (docosahexaenoic acid) was dissolved in 25 ml dimethyl formamide (DMF). 1 mg reduced sesame pigment (Example 1) and 1 mg arginine were dissolved in 10 ml deionized water. 5 ml of the DHA solution was placed into a small cuvette along with 1 ml sesame pigment solution and 1 ml of 1% $H_2O_2$.

A blank sample was prepared as above without addition of the reduced sesame pigment solution.

The two cuvettes were sealed for 16 hours. Samples were removed and analyzed by gas phase chromatography to determine the residual ratio of DHA.

The residual ratio of DHA in samples are presented in the table below.

| Sample name | Residual ratio of DHA/% |
|---|---|
| Blank Sample | 76.0 |
| Reduced sesame pigment | 98.1 |

Example 7

The following example indicates the reduced sesame pigment can protect phosphorylcholine (PC) from degradation.

25 mg phosphorylcholine (PC) was dissolved in 25 ml dimethyl formamide (DMF). 1 mg of reduced sesame pigment (Example 1) and 1 mg arginine were dissolved in 10 ml deionized water. 5 ml of the PC solution was placed in a small cuvette along with 1 ml reduced sesame pigment solution and 1 ml 1% hydrogen peroxide.

A blank sample was prepared as above without addition of the reduced sesame pigment solution.

The two cuvettes were sealed and left for 16 hours. Samples were analyzed by HPLC-ELSD to determine the residual ratio of PC.

The residual ratios of phosphorylcholine in the samples are presented in the table below.

| Sample name | Residual ratio of PC/% |
|---|---|
| Blank Sample | 70.9 |
| Reduced sesame pigment | 85.5 |

Example 8

The following example indicates that the reduced sesame pigment can protect the combination of Coenzyme Q10 and DHLA (dihydrolipoic acid).

It has been discovered that DHLA can protect Coenzyme Q10, which was described in Austrian patent AT 504148 A1, U.S. provisional application 60/886,395, U.S. utility 11/843,935 and PCT/IB2007/003623, the contents of which are incorporated herein in their entirety.

Surprisingly, it has been found that the reduced sesame pigment could remarkably increase the protective effect of Coenzyme Q10 from DHLA.

To a small flask was added 10 ml deionized water, 30 ml ethanol and 10 ml tetrahydrofuran (THF). 3 mg coenzyme Q10 and 5 mg dihydrolipoic acid (DHLA) were added to the solution and sonicated to fully dissolve the coenzyme Q10.

5 mg reduced sesame pigment (Example 1) and 3 mg potassium hydroxide were added to 5 ml deionized water. 1 ml sesame pigment solution was added to the coenzyme Q10 solution. The solution was sonicated for 5 minutes and analyzed by HPLC (Agilent 1100) for the ratio of reduced form coenzyme Q10 to non-reduced coenzyme Q10.

A blank sample was prepared as above without the reduced sesame pigment present.

The ratios of reduced Coenzyme Q10 in samples are presented in the table below.

| Sample name | Ratio of reduced coenzyme Q10/% |
|---|---|
| Blank Sample | Cannot detected |
| Sesame pigment sample | 97.4 |

The DHLA in the present example can be replaced by other reducing agents, like Vitamin C.

Example 9

Determination of Sesame Pigments with UV-VIS Absorption

Sample Purification

A 2 g pigment sample was extracted with 50 ml chloroform, 50 ml acetone and 50 ml ethanol successively. The sample was vacuum dried at room temperature. 1 g of sesame pigment was dissolved in 1.0 g sodium hydroxide and 30 ml de-ionized water. About 25 ml chloroform and 5 ml n-butanol were added to the mixture, the resultant mixture was shaken thoroughly, then centrifuged to separate the lower layer and filtered. The aqueous layer was washed with 1% sodium hydroxide solution. All filtrates were combined and the pH value was adjusted to a pH of 3 with HCl. The material was filtered and the resultant cake was washed with deionized water until the pH of the filtrate was about 6. The solid cake was vacuum dried to obtain purified pigment.

The whole process was conducted with temperature control; the liquid temperature was not allowed to reach to 25° C. or higher and it was found best to perform the reactions with an inert gas.

Method 20 mg sesame pigment and 1.0 g sodium hydroxide were dissolved in a 100 ml volumetric flask. The mixture was sonicated for 10 minutes and the flask was will to volume with de-ionized water. A 2 ml sample was transferred to a 10 ml volumetric flask and filled to volume with de-ionized water. The UV-VIS absorbance of final solution was measured at 500 nm.

Results

| Sample Name | UV absorbance |
| --- | --- |
| Origin pigment (No reduction) | 0.168 |
| Product of Example 1 | 0.151 |
| Product of Example 2 | 0.132 |
| Product of Example 3 | 0.124 |
| Product of Example 4 | 0.118 |

Application Effectiveness

| Sample Name | Residual ratio of lutein/% |
| --- | --- |
| Origin pigment (No reduction) | 80.1 |
| Product of Example 1 | 81.7 |
| Product of Example 2 | 85.9 |
| Product of Example 3 | 92.0 |
| Product of Example 4 | 94.9 |

Conditions were identical as those in Example 5.

Example 10

The Effect of Sesame Extract on the Oxidation of LDL

Human LDLs were obtained by ultracentrifugation from fresh human blood, followed by dialysis against in 10 mM PBS (pH 7.4) at 4° C. in the dark for 24 h. LDLs were mixed with different amounts sesame pigment (dissolved in PBS, pH=7.4, by ultrasonication) (0, 10, 50, 100, 250, 500 µg/mL respectively). Sesame extract was obtained by the method given in Appendix 1, oxidation and reduction was performed as given in Appendix 1. Reaction was initiated by adding a solution of CuSO4 (10 µM); samples were then incubated at 37° C. for 3 hours. The formation of conjugated dienes was measured at 234 nm using a UV/VIS spectrophotometer.

Data evaluation was performed by comparison of the slope of increase in diene-formation. The steepest slope (i.e. without addition of anti-oxidants) was set to 100%. Results are given as relative %±s.d. (n=3).

The lag-time until start of diene formation was estimated from the kinetic curves obtained. Results are given in minutes.

The plateau-concentration of dienes formed was obtained using a molar extinction coefficient of 29500 $M^{-1} \cdot cm^{-1}$. Results are given as µmol dienes formed/mg LDL-protein.

Figure 4:
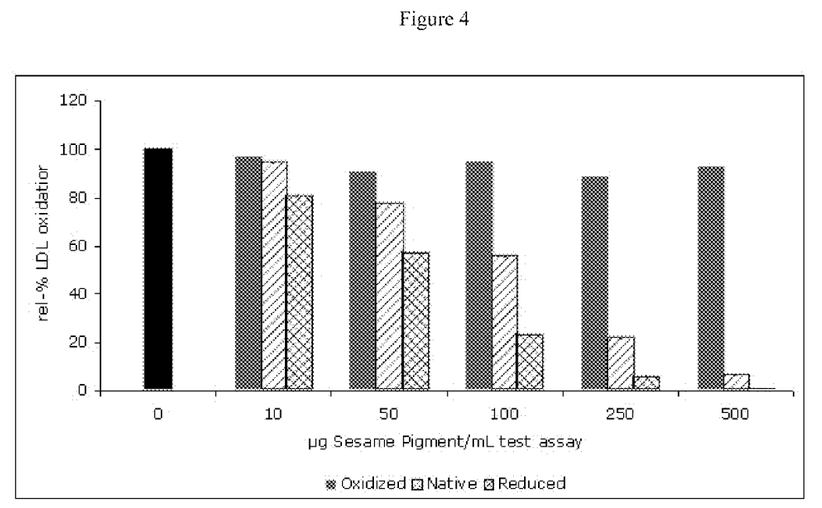
FIG. 4 depicts LDL-oxidation in presence of sesame extract.

As seen in FIG. 4, native or reduced sesame pigment inhibited LDL-oxidation whereas oxidized sesame pigment showed almost no effect.

Figure 5:
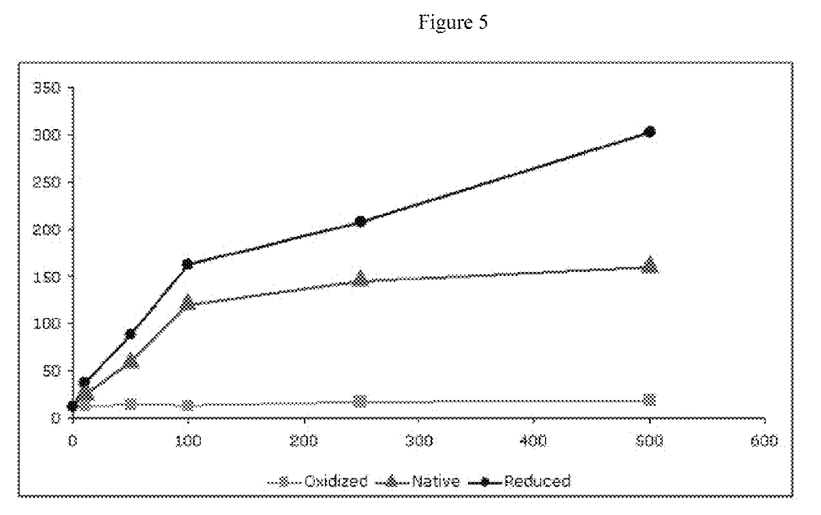
FIG. 5 provides dose-dependent lag time shifts of oxidized, native and reduced sesame extracts of Example 10 at varying concentrations.

As seen in FIG. 5, the lag time to the start of LDL-oxidation shows a dose-dependency for reduced pigment. The native pigment showed a saturable effect around 100 µg/ml and the oxidized pigment yielded almost no effect.

[OK?]

The potency of reduced sesame pigment was at all concentrations tested significantly stronger than that of native pigment.

Reduced sesame pigment is a potent inhibitor of LDL-oxidation and may act in-vivo as preventive agent for arteriosclerosis (plaque formation of oxidized LDLs).

APPENDIX 1

Preparation of Pigment Sample

Approximately 30 g Sesame seed were finely grinded and cooked in approximately 25% (m/m) HCl for 1 hour. Thereafter, the residue was collected by filtration and dried at 105° C. The dry residue was extracted in a Soxhlet extractor for 3 hours (150 ml petrol ether) to remove the fat.

The residue was then dried at 75° C. for 2 hours (residue about 20 g). The residue was subjected to protein digestion by addition of 0.50 g $NaH_2PO_4$ and 0.2 g EDTA. The mixture was made up to 200 mL by addition of water, the pH was adjusted to 7.4. Thereafter 100 mg trypsin (110.000 IU/mg) were added and the mixture was stirred at room temperature for 12 hours.

The pH of the mixture was then adjusted to ≦3.0 with HCl and stirred for a further 4 hours and the precipitate was collected by centrifugation (30 minutes 5000 g).

The precipitate was then suspended in 200 mL water/$NH_4OH$ (pH=10.5) and stirred for 2 hours at room temperature. The suspension was then filtered to remove non-dissolved material. The filtrate was acidified to pH 2.0-2.5. (HCl) and stirred for 4 hours at room temperature. The precipitate was collected by filtration. The precipitate was washed for several times with 0.01 M HCl and 1 time with hot water. The residue was collected and dried over night at 60° C., followed by storage over $P_2O_5$ to remove traces of water. The sample collected weighed 725 mg.

Based on spectrophotometric evaluation the sample contained 33% melanin when compared to sepia melanin standard. Melanin is isolated from the ink sac of *Sepia officinalis* (*Sepia* melanin) and has been proposed as a standard for natural eumelanin. It is a commercial product: M2649 (Sigma-Aldrich).

Reduction of Sesame Pigment

Sesame pigment was reduced by treatment with $Ti^{3+}$ according to a previously described procedure (Horak & Gillette, 1971). 100 mg of sesame pigment, suspended in water, was combined with a 20 ml solution containing 0.1 M sodium oxalate and 1 M sulfuric acid. Then, 5 ml of 80 mM $TiCl_3$ dissolved in dilute sulfuric acid (1:10 by volume) was added. This mixture was incubated for 120 min, and the reduced pigment was separated by centrifugation. The precipitate was washed with diluted sulfuric acid and of water. Finally, the reduced pigment was dialyzed against milli-Q water for 24 h. The reduced samples were suspended in distilled water, and 0.1 M NaOH was added dropwise to adjust pH to 7.5. The solutions thus obtained were filtered through a Nalgene 0.45-mm syringe filter. All operations were conducted under $N_2$.

The reduced sample is denominated as "reduced pigment" in Example 10 and FIGS. 4 and 5.

The plateau amount of dienes formed provided results as shown in Tables 1-3.

TABLE 1

Diene formation with reduced sesame Pigment

| μg/mL Assay | (μmol diene/mg protein) × 10³ |
|---|---|
| 0.0 | 9.08 |
| 10.0 | 7.36 |
| 50.0 | 4.27 |
| 100.0 | 2.91 |
| 250.0 | 1.91 |
| 500.0 | 0.91 |

TABLE 2

Diene formation with native sesame Pigment

| μg/mL Assay | (μmol diene/mg protein) × 10³ |
|---|---|
| 0.0 | 9.08 |
| 10.0 | 7.90 |
| 50.0 | 6.17 |
| 100.0 | 5.90 |
| 250.0 | 3.90 |
| 500.0 | 4.27 |

TABLE 3

Diene formation with oxidized sesame Pigment

| μg/mL Assay | (μmol diene/mg protein) × 10³ |
|---|---|
| 0.0 | 9.08 |
| 10.0 | 8.45 |
| 50.0 | 8.08 |
| 100.0 | 8.26 |
| 250.0 | 7.36 |
| 500.0 | 8.08 |

As noted above, the effect of reduced pigment was stronger than that of native pigment and, again, the oxidized pigment yielded no effect.

Oxidation of Pigment

To further support the effect of the oxidation/reduction on the properties of the pigment, sesame pigment was subjected to oxidation.

100 mg of sesame pigment were dissolved in 20 ml water made up to pH=11.0 with NaOH. The solution was stirred at 40° C. for 24 hours in a sealed vial which was connected to an pump delivering air to the solution. Additionally 3 portions of 1 ml $H_2O_2$ solution (3% m/m) were added. Finally the oxidized product was collected by acidification to pH=2.0 with HCl, centrifugation and collection by filtration. After thorough washing with hot water, the oxidized pigment was dialyzed against milli-Q water for 24 h. The oxidized samples were suspended in distilled water, and 0.1 M NaOH was added dropwise to adjust pH to 7.5. The solutions thus obtained were filtered through a Nalgene 0.45-mm syringe filter.

The oxidized sample is denominated as "oxidized pigment" in Example 10 and FIGS. 4 and 5.

Oxidative Degradation of Ascorbic Acid (Vitamin C)

5 mg ascorbic acid were dissolved in 0.01 M phosphate-buffer pH=7.5 to a final volume of 10 ml. 2 mg sesame pigment (native or reduced sample Example 4, above) were added to the ascorbic acid solution and dissolved by ultra-sonication.

At selected time points (up to 96 hours), 0.5 ml samples were drawn from and diluted 1:10 with phosphoric acid (pH=2.5). The pigment containing samples were cleared by centrifugation and injected on a HPLC-System calibrated for ascorbic acid determination.

Figure 6:
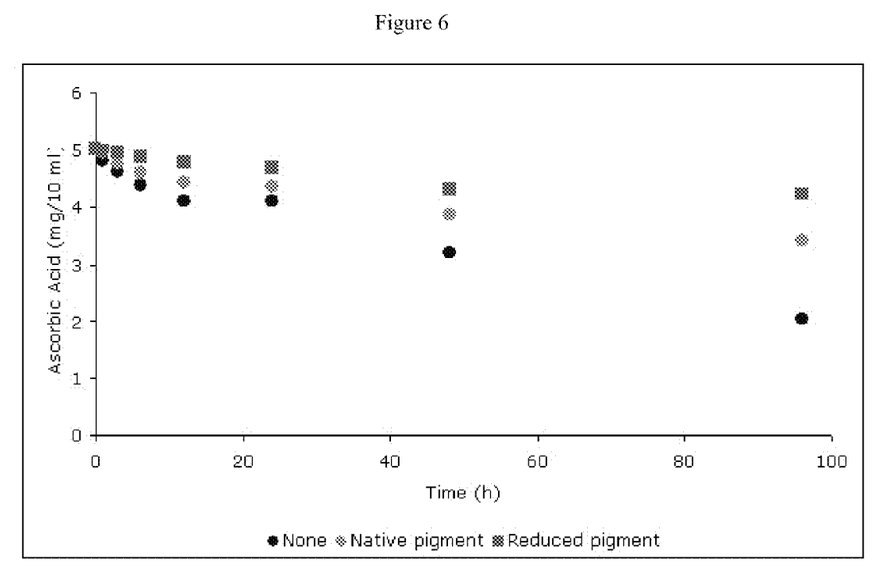
FIG. 6 provides graphical representation of protection of ascorbic acid degradation by sesame extract (reduced or native).

As is demonstrated by FIG. 6, reduced sesame pigment protects ascorbic acid from degradation. Moreover, the reduced sesame pigment is more effective than that of native sesame pigment.

Reduced sesame extract acts as stabilizing agent for ascorbic acid. In-vivo sesame pigment may exert a vitamin C sparing effect by increasing its stability or by recycling.

The following paragraphs enumerated consecutively from one (1) through 79 provide for various aspects of the present invention. In one embodiment, in a first paragraph (1), the present invention provides a pigment comprising a reduced melanin wherein the molecular weight of the reduced melanin is between about 264 and about 5400 daltons, wherein the carbon content of the reduced melanin is between about 49 percent and about 57 percent by weight, the hydrogen content of the reduced melanin is between about 5 percent and about 10 percent by weight and the oxygen content of the reduced melanin is between about 33 percent and about 37 percent by weight, wherein the ratio of hydroxyl to carbonyl quinone content of the reduced melanin is at least 50 percent on a molar basis.

2. The pigment of paragraph 1, wherein the reduced melanin is derived from a seed shell or hull.

3. The pigment of either of paragraphs 1 or 2, wherein the seed shell or hull is from a sesame seed.

4. The pigment of any of paragraphs 1 through 3, wherein the nitrogen content of the reduced melanin is between about 5 percent and about 10 percent by weight.

5. The pigment of any of paragraphs 1 through 4, wherein the sulfur content of the reduced melanin is less than about 1 percent by weight.

6. The pigment of any of paragraphs 1 through 5, wherein infrared spectra of the reduced melanin exhibits absorption bands at about 3400 cm⁻¹, at about 2950 cm⁻¹, at about 1600 to about 1650 cm⁻¹, at about 1380 to about 1400 cm⁻¹, at about 1260 cm⁻¹ and at about 1170 cm⁻¹.

7. The pigment of any of paragraphs 1 through 6, wherein the hydroxyl content to carbonyl content molar percentage ratio is at least 60 percent.

8. The pigment of any of paragraphs 1 through 7, wherein the molecular weight range of the reduced melanin is between about 264 and about 2000 daltons.

9. The pigment of any of paragraphs 1 through 8, wherein the molecular weight range of the reduced melanin is between about 400 and about 1600 daltons.

10. A method to prepare a reduced melanin pigment comprising the steps:
   a) mixing an aqueous base and pulverized sesame seed at an elevated temperature followed by cooling of the black mixture to room temperature;
   b) filtering the mixture and rinsing with water to provide a filtrate;
   c) treating the filtrate with an aqueous acid; and
   d) adding a reducing agent to the filtrate until evolution of gas ceases and the reduced melanin pigment is formed.

11. The method of paragraph 10, wherein the concentration of the base in the aqueous base in step a) is between about 0.5 percent and about 2 percent by weight.

12. The method of either of paragraphs 10 or 11, wherein the base is sodium hydroxide.

13. The method of any of paragraphs 10 through 12, wherein ratio of aqueous base to sesame seed is about 5:1 on a weight basis.

14. The method of any of paragraphs 10 through 13, wherein the elevated temperature of step a) is between about 40° C. and about 80° C.

15. The method of paragraph 14, wherein the temperature is 60° C.

16. The method of any of paragraphs 10 through 15, wherein the mixture is heated for between about 0.5 hours and about 5 hours.

17. The method of paragraph 16, wherein the mixture is heated for about 3 hours.

18. The method of any of paragraphs 10 through 17, wherein the treated filtrate of step c) is agitated prior to addition of the reducing agent.

19. The method of any of paragraphs 10 through 18, wherein the reducing agent is added to the filtrate of step d) at temperature between about 10° C. and about 35° C.

20. The method of paragraph 19, wherein the temperature of the filtrate is about 25° C.

21. The method of any of paragraphs 10 through 20, wherein the reduced melanin pigment comprises a reduced melanin wherein the molecular weight of the reduced melanin is between about 264 and about 5400 daltons, wherein the carbon content of the reduced melanin is between about 49 percent and about 57 percent by weight, the hydrogen content of the reduced melanin is between about 5 percent and about 10 percent by weight and the oxygen content of the reduced melanin is between about 33 percent and about 37 percent by weight, wherein the ratio of hydroxyl to carbonyl quinone content of the reduced melanin is at least 50 percent on a molar basis.

22. The method of any of paragraphs 10 through 21, wherein the nitrogen content of the reduced melanin is between about 5 percent and about 10 percent by weight.

23. The method of any of paragraphs 10 through 22, wherein the sulfur content of the reduced melanin is less than about 1 percent by weight.

24. The method of any of paragraphs 10 through 23, wherein infrared spectra of the reduced melanin exhibits absorption bands at about 3400 $cm^{-1}$, at about 2950 $cm^{-1}$, at about 1600 to about 1650 $cm^{-1}$, at about 1380 to about 1400 $cm^{-1}$, at about 1260 $cm^{-1}$ and at about 1170 $cm^{-1}$.

25. The method of any of paragraphs 10 through 24, wherein the hydroxyl content to carbonyl content molar percentage ratio is at least 60 percent.

26. The method of any of paragraphs 10 through 25, wherein the molecular weight range of the reduced melanin is between about 264 and about 2000 daltons.

27. The method of any of paragraphs 10 through 26, wherein the molecular weight range of the reduced melanin is between about 400 and about 1600 daltons.

28. A method to prepare a reduced melanin pigment comprising the steps:
  a) mixing an aqueous base and pulverized sesame seed at or below room temperature;
  b) filtering the mixture and rinsing with water to provide a filtrate;
  c) treating the filtrate with an aqueous acid at or below room temperature to a pH of between about 1 and below about 7; and
  d) collecting the reduced melanin pigment.

29. The method of paragraph 28, wherein the concentration of the base in the aqueous base in step a) is between about 0.5 percent and about 2 percent by weight.

30. The method of either of paragraphs 28 or 29, wherein the base is sodium hydroxide.

31. The method of any of paragraphs 28 through 30, wherein ratio of aqueous base to sesame seed is about 5:1 on a weight basis.

32. The method of any of paragraphs 28 through 31, wherein the temperature of the mixture of step a) is maintained below a temperature of about 35° C.

33. The method of any of paragraphs 28 or 32, wherein the mixture of step a) is mixed for between about 5 hours and about 48 hours.

34. The method of paragraph 33, wherein the mixture is mixed for about 24 hours.

35. The method of any of paragraphs 28 through 34, wherein the aqueous acid of step c) is about 15% acid by volume.

36. The method of any of paragraphs 28 through 35, wherein the acid of step c) is hydrochloric acid.

37. The method of any of paragraphs 28 through 36, wherein the temperature of the filtrate of step c) is maintained between about 10° C. and about 25° C.

38. The method of paragraph 37, wherein the temperature of the filtrate of step c) is maintained at about 25° C.

39. The method of any of paragraphs 28 through 38, wherein the pH of the filtrate of step c) is about a pH of 1.

40. The method of any of paragraphs 28 through 39, wherein the reduced melanin pigment is collected by centrifugation.

41. The method of any of paragraphs 28 through 40, wherein the reduced melanin pigment comprises a reduced melanin wherein the molecular weight of the reduced melanin is between about 264 and about 5000 daltons, wherein the carbon content of the reduced melanin is between about 49 percent and about 57 percent by weight, the hydrogen content of the reduced melanin is between about 5 percent and about 10 percent by weight and the oxygen content of the reduced melanin is between about 33 percent and about 37 percent by weight, wherein the ratio of hydroxyl to carbonyl quinone content of the reduced melanin is at least 50 percent on a molar basis.

42. The method of any of paragraphs 28 through 41, wherein the nitrogen content of the reduced melanin is between about 5 percent and about 10 percent by weight.

43. The method of any of paragraphs 28 through 42, wherein the sulfur content of the reduced melanin is less than about 1 percent by weight.

44. The method of any of paragraphs 28 through 43, wherein infrared spectra of the reduced melanin exhibits absorption bands at about 3400 $cm^{-1}$, at about 2950 $cm^{-1}$, at about 1600 to about 1650 $cm^{-1}$, at about 1380 to about 1400 $cm^{-1}$, at about 1260 $cm^{-1}$ and at about 1170 $cm^{-1}$.

45. The method of any of paragraphs 28 through 44, wherein the hydroxyl content to carbonyl content molar percentage ratio is at least 60 percent.

46. The method of any of paragraphs 28 through 45, wherein the molecular weight range of the reduced melanin is between about 264 and about 2000 daltons.

47. The method of any of paragraphs 28 through 46, wherein the molecular weight range of the reduced melanin is between about 400 and about 1600 daltons.

48. A pigment comprising the formula:

(I)

wherein each X, of each m and n unit, independently, can be either a COOH or salt thereof or a hydrogen atom;

wherein at least one of each $Y^1$ or each $Y^2$, of each m and n unit, independently, is an NH and the other is a CH provided both $Y^1$ and $Y^2$ are not both NH or CH;

wherein each $Q^1$ and $Q^2$, of each m and n unit, are each independently, a hydroxyl, a hydroxyl anion, a H, or a =O;

provided that the molar ratio of hydroxyl to ketone functionality within the reduced melanin is greater than 50 percent;

wherein ===== represents a conjugated π system;

wherein m is from 1 to about 40;

wherein n is from 1 to about 40;

wherein m+n=from 2 to about 40; and wherein each m and n monomeric unit can be the same or different.

49. The pigment of paragraph 48, wherein the nitrogen content of the reduced melanin is between about 5 percent and about 10 percent by weight.

50. The pigment of either of paragraphs 48 or 49, wherein the sulfur content of the reduced melanin is less than about 1 percent by weight.

51. The pigment of any of paragraphs 48 through 50, wherein infrared spectra of the pigment exhibits absorption bands at about 3400 cm$^{-1}$, at about 2950 cm$^{-1}$, at about 1600 to about 1650 cm$^{-1}$, at about 1380 to about 1400 cm$^{-1}$, at about 1260 cm$^{-1}$ and at about 1170 cm$^{-1}$.

52. The pigment of any of paragraphs 48 through 51, wherein the hydroxyl content to carbonyl content molar percentage ratio is at least 60 percent.

53. The pigment of any of paragraphs 48 through 52, wherein the molecular weight range of pigment is between about 264 and about 2000 daltons.

54. The pigment of any of paragraphs 48 through 53, wherein the molecular weight range of pigment is between about 400 and about 1600 daltons.

55. The method of paragraph 10, wherein the pigment comprises any of paragraphs 48 through 54.

56. The method of paragraph 28, wherein the pigment comprises any of paragraphs 48 through 54.

57. The pigment of paragraph 48, wherein n=1.

58. The pigment of paragraph 48, wherein at least two different monomeric units are selected from:

59. The pigment of paragraph 48, wherein one monomeric unit is selected from:

-continued

60. A method to treat or prevent one or more of the following conditions: maintain or increase lutein concentration in an eye, maintain visual acuity, to decrease free radicals in a physiological state, to help promote nerve, brain, or marrow health, for degenerative diseases of the nervous system, including Parkinson's disease or Alzheimer's disease, or as for skin protection such as for UV protection.

61. A plant food nutritive supplement comprising any of paragraphs 1 through 9 or 48 through 54, or 57 through 59 and a carrier.

62. A food or beverage, comprising an edible material or a consumable liquid and the pigment of any of paragraphs 1 through 9 or 48 through 54 or 57 through 59.

63. The food of paragraph 62, wherein the food is ice-cream or yogurt.

64. A method to prevent or reduce the degradation of lutein, coenzyme Q10 with DHLA, DHA, or phosphorylcholine comprising treating any of the aforementioned materials with the pigment of any of claims 1 through 9 or 48 through 54 or 57 through 59.

65. A hair supplement for blackening hair, comprising the pigment of any of paragraphs 1 through 9 or 48 through 54 or 57 through 59 and an acceptable carrier.

66. A method to enhance or maintain cognition in a subject by providing the pigment of any of paragraphs 1 through 9, or 48 through 54 or 57 through 59.

67. A composition comprising a sesame extract comprising a UV-VIS absorbance value of about 0.10 to about 0.16 at 500 nm at a concentration of 0.04 mg/ml in an aqueous solution.

68. The composition according to paragraph 67, wherein the molecular weight of the reduced melanin is between about 264 and about 5400 Daltons.

69. The composition according to either paragraphs 67 or 68, wherein the carbon content of the reduced melanin is from about 35 to about 57 percent by weight, the hydrogen content is from about 5 to about 10 percent by weight and the nitrogen content is from about 5 to about 10 percent by weight.

70. The composition according to any of paragraphs 67 through 69, wherein the sulfur content of the reduced melanin is less than about 1 percent by weight.

71. The composition according to any of paragraphs 67 through 70, wherein infrared spectra of the reduced melanin exhibits absorption bands at about 3400 $cm^{-1}$, at about 2950 $cm^{-1}$, at about 1600 to about 1650 $cm^{-1}$, at about 1380 to about 1400 $cm^{-1}$, at about 1260 $cm^{-1}$ and at about 1170 $cm^{-1}$.

72. The composition according to any of paragraphs 67 and 69 through 71, wherein the molecular weight of the reduced melanin is between about 264 and about 2000 Daltons.

73. The composition according to paragraphs 67 and 69 through 71, wherein the molecular weight of the reduced melanin is between about 400 and about 1600 Daltons.

74. A method to prevent or reduce oxidation of a vitamin comprising the step of combining a sufficient amount of any of the compositions of paragraphs 67 through 73 and a vitamin.

75. The method of paragraph 74, wherein the vitamin is vitamin C.

76. A method to reduce or inhibit the oxidation of LDL, comprising providing to a subject in need thereof, a sufficient amount of any of the composition of paragraphs 67 through 73 to LDL to reduce or inhibit the oxidation of LDL.

77. A method to treat or prevent cardiovascular diseases, comprising providing to a subject in need thereof, a therapeutically effective amount of any of the composition of paragraphs 67 through 73 to treat or prevent a cardiovascular disease.

78. The method of paragraph 77, wherein the cardiovascular disease is atherosclerosis or coronary artery disease.

79. A method to treat or prevent ulceration, comprising providing to a subject in need thereof, a therapeutically effective amount of any of the composition of paragraphs 67 through 73 to treat or prevent ulceration.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A composition comprising a reduced melanin extracted from sesame seed hulls or sesame seed shells, wherein the molecular weight of the reduced melanin is between about 264 daltons and about 5000 daltons, wherein the carbon content of the reduced melanin is between about 49 percent and about 57 percent by weight, the hydrogen content of the reduced melanin is between about 5 percent and about 10 percent by weight and the oxygen content of the reduced melanin is between about 33 percent and about 37 percent by weight, wherein
the reduced melanin comprises a formula:

(I)

wherein each X, of each m and n unit, independently, can be either a COOH or salt thereof or a hydrogen atom;
wherein at least one of each $Y^1$ or each $Y^2$, of each m and n unit, independently, is an NH and the other is a CH provided both $Y^1$ and $Y^2$ are not both NH or CH;

wherein each $Q^1$ and $Q^2$, of each m and n unit, are each independently, a hydroxyl, a hydroxyl anion, a H, or a =O;

provided that the molar ratio of hydroxyl to ketone functionality within the reduced melanin is greater than 50 percent;

wherein ===== represents a conjugated π system;

wherein m is from 1 to about 40;

wherein n is from 1 to about 40;

wherein m+n=from 2 to about 40; and wherein each m and n monomeric unit can be the same or different.

2. The composition of claim 1, wherein the nitrogen content of the reduced melanin is between about 5 percent and about 10 percent by weight.

3. The composition of claim 1, wherein the nitrogen content of the reduced melanin is between about 5 percent and about 10 percent by weight.

4. The composition of claim 1, wherein the sulfur content of the reduced melanin is less than about 1 percent by weight.

5. The composition of claim 1, wherein infrared spectra of the pigment exhibits absorption bands at about 3400 cm$^{-1}$, at about 2950 cm$^{-1}$, at about 1600 to about 1650 cm$^{-1}$, at about 1380 to about 1400 cm$^{-1}$, at about 1260 cm$^{-1}$ and at about 1170 cm$^{-1}$.

6. The composition of claim 1, wherein the hydroxyl content to carbonyl content molar percentage ratio is at least 60 percent.

7. The composition of claim 1, wherein the molecular weight range of pigment is between about 264 daltons and about 2000 daltons.

8. The composition of claim 1, wherein the molecular weight range of pigment is between about 400 daltons and about 1600 daltons.

9. The composition of claim 1, wherein n=1.

10. The composition of claim 1, wherein at least two different monomeric units are selected from the group consisting of:

11. The composition of claim 1, wherein one monomeric unit is selected from the group consisting of:

12. The composition of claim 1, wherein the ratio of hydroxyl to carbonyl quinone content of the reduced melanin is at least 50 percent on a molar basis.

13. The composition of claim 1, wherein the composition comprises a UV-VIS absorption value of about 0.10 to about 0.16 at 500 nm at a concentration of 0.04 mg/ml in an aqueous solution.

* * * * *